(12) United States Patent
Manning et al.

(10) Patent No.: US 8,138,939 B2
(45) Date of Patent: Mar. 20, 2012

(54) DRUG DISPENSER/CONTAINER DISPLAY

(75) Inventors: William Manning, Fairport, NY (US); Sarah Kwon, Kent, OH (US); Albert Green, Kent, OH (US); Joel Domino, Aurora, OH (US); Asad Khan, Kent, OH (US); J. William Doane, Kent, OH (US)

(73) Assignee: Manning Ventures, Inc., Fairport, NY (US)

( * ) Notice: Subject to any disclaimer, the term of this patent is extended or adjusted under 35 U.S.C. 154(b) by 536 days.

(21) Appl. No.: 12/178,232

(22) Filed: Jul. 23, 2008

(65) Prior Publication Data
US 2009/0051560 A1 Feb. 26, 2009

Related U.S. Application Data (60) Provisional application No. 60/961,739, filed on Jul. 24, 2007, provisional application No. 60/961,781, filed on Jul. 24, 2007, provisional application No. 60/969,752, filed on Sep. 4, 2007.

(51) Int. Cl.
*G08B 5/00* (2006.01)
(52) U.S. Cl. ............. 340/815.4; 340/309.16; 340/309.7; 368/1; 368/10; 368/108; 368/244
(58) Field of Classification Search ............... 340/815.4, 340/815.16; 368/1, 10, 108, 244
See application file for complete search history.

(56) References Cited

U.S. PATENT DOCUMENTS

| | | | |
|---|---|---|---|
| 4,367,955 A | 1/1983 | Ballew |
| 4,382,688 A | 5/1983 | Machamer |
| 4,448,541 A | 5/1984 | Wirtschafter |
| 4,725,997 A | 2/1988 | Urquhart et al. |
| 4,748,600 A | 5/1988 | Urquhart |
| 4,939,705 A | 7/1990 | Hamilton et al. |
| 4,971,221 A | 11/1990 | Urquhart et al. |
| 5,079,006 A | 1/1992 | Urquhart |
| 5,852,590 A | 12/1998 | de la Huerga |
| 5,917,429 A | 6/1999 | Otis et al. |
| 5,953,288 A | 9/1999 | Chappell |
| 6,102,855 A | 8/2000 | Kehr et al. |
| 6,259,654 B1 | 7/2001 | de la Huerga |
| 6,268,839 B1 * | 7/2001 | Yang et al. ................ 345/89 |

(Continued)

FOREIGN PATENT DOCUMENTS
GB 2265142 A 9/1993
(Continued)

OTHER PUBLICATIONS

"Automatic Pill Dispenser from e-pill", source: http://www.epill.com/dispenser.html?source=google.

(Continued)

*Primary Examiner* — George Bugg
*Assistant Examiner* — Ojiako Nwugo
(74) *Attorney, Agent, or Firm* — Pearne & Gordon LLP (57) ABSTRACT

A display for use on medical dispensing equipment, and the resulting medical device and its method of display. In particular, provided are a number of specific embodiments of such a display on a medical device, including a film display for use on pill bottles and pill dispensers that utilize colored images as a dosage reminder for the user, a conformable bistable reflective display for use on drug delivery devices, and a conformable bistable reflective display for use on blood glucose meters.

32 Claims, 3 Drawing Sheets

U.S. PATENT DOCUMENTS

| | | |
|---|---|---|
| 6,324,123 B1 | 11/2001 | Durso |
| 6,545,592 B2 | 4/2003 | Weiner |
| 6,604,019 B2 | 8/2003 | Ahlin et al. |
| 6,662,081 B1 | 12/2003 | Jacober et al. |
| 6,819,310 B2 | 11/2004 | Huang et al. |
| 7,236,151 B2 | 6/2007 | Doane et al. |
| 7,554,434 B1 * | 6/2009 | Gifford et al. ........... 340/309.16 |
| 2001/0009398 A1 | 7/2001 | Sekura et al. |
| 2002/0169635 A1 | 11/2002 | Shillingburg |
| 2003/0043026 A1* | 3/2003 | Noble et al. ............. 340/309.15 |
| 2005/0150805 A1 | 7/2005 | Burchell |
| 2005/0252924 A1 | 11/2005 | Pieper et al. |
| 2006/0049380 A1 | 3/2006 | Sha et al. |
| 2006/0055650 A1 | 3/2006 | Kwok et al. |
| 2006/0187003 A1* | 8/2006 | Terenna ................... 340/309.16 |
| 2006/0218015 A1* | 9/2006 | Walker et al. ..................... 705/3 |
| 2007/0064541 A1* | 3/2007 | Kagan .......................... 368/108 |
| 2007/0164980 A1* | 7/2007 | Manning ..................... 345/104 |

FOREIGN PATENT DOCUMENTS

| | | |
|---|---|---|
| WO | 03051721 A2 | 6/2003 |
| WO | 2004073498 A2 | 2/2004 |

OTHER PUBLICATIONS

"ForgettingthePill.com personal reminder products", source: http://www.forgettingthepill.com/timers.html.

"VRI Right Pill, Right Dose, Right Time", source: http://www.monitoringcare.com/medready.html.

* cited by examiner

DRUG DISPENSER/CONTAINER DISPLAY

CROSS-REFERENCES TO RELATED APPLICATIONS

This application claims the benefit of U.S. provisional application Ser. Nos. 60/961,739 (filed on Jul. 24, 2007), 60/961,781 (filed on Jul. 24, 2007), and 60/969,752 (filed on Sep. 4, 2007), all incorporated herein by reference.

FIELD OF THE INVENTION

Disclosed is a display for use on medical dispensing equipment. In particular, disclosed are a number of specific embodiments of such a display, including a film display for use on pill bottles and pill dispensers that utilizes colored images as a dosage reminder for the user, a conformable bistable reflective display for use on drug delivery devices, and a conformable bistable reflective display for use on blood glucose meters.

The low power, thin display conforms to the shape of the container to provide the user with updatable content information in large readable fonts and color while maintaining the small size, shape, low weight, ruggedness of the delivery device for ease in carrying and handling. A thin electronically updateable display in the form of a flexible film can be cemented or otherwise attached to a pill container or a container cap without adding significant weight and volume to the container. The display can provide images that change color to provide such information as when the last dosage was taken, when it is time to take the next dosage, when it is time for a refill, and other information as might be useful to a user.

BACKGROUND OF THE INVENTION

A problem with many pharmaceuticals is the timely self-administration of drugs. Many drugs are self administered by the drug user and the user forgets if he has taken a pill on schedule. Complicating the problem is that there is usually more than one pill, often as many as seven or eight, some of which some are taken at different times from different bottles. Many users have no system for keeping track of the pills they have taken or need to take. They often take the pills directly from the bottle each time a pill is taken. Pill bottles are filled at the pharmacy; the bottles being simply containers with a week, month or longer supply. When the user takes the pills directly from the bottle there is no convenient means of keeping track of daily or hourly usage. Most users are aged people with failing memory and eye sight adding to the problem.

The lack of adherence to the prescribed medication regimen is a common, well recognized problem that increases overall healthcare costs. Developing tools that can really aid or address this problem will have a huge impact on the well-being of patients and reduction of healthcare costs to all.

It would therefore be useful to provide a simple film display of sufficiently low cost for a container of pharmaceutical drugs where changing color and symbols are the primary reminder means for taking the drug. The display is electronically updated as a reminder using numerical and other readouts to inform the user. The display is flexible to conform to the shape of the container or container cap so as not to significantly alter the shape, size and weight of the container.

In addition, there are many drugs in today's market that deliver oral medications by a metered dose inhalation of aerosolized liquid or by breath-actuated dry powder inhalation. These drugs come in a small, hand held, easily transportable container containing many doses; used over a period of time until the container is empty and needs replacement. An example of an aerosolized dispenser is the metered dose inhaler (MDI) device that delivers measured amount of medications orally in aerosolized dosage form, in a pressurized metal delivery container. Each canister is supplied with a plastic oral actuator that is not interchangeable. Examples include Albuterol, Atrovent, Combivent, Qvar, Flovent; each containing a different class of drugs (bronchodilators and corticosteroids) in similar dosage forms. The dosages of these drugs are metered by a small display that counts each time the inhaler is used. This is the means used to determine when the canister is near empty and needs replacing.

In some other inhaler drugs another method, the "float test" has been used in determining the amount of drug remaining in the canister. In the "float test" the weight of the canister and its contents is determined by how it floats in water. The MDI metal canisters, however, can not be submerged into water in order to use the "float test" to determine the remaining amount of medications, as (HFA) hydrofluoroalkane propellants in the aerosolized medications are not compatible with the water submersion method.

Dry powder dosage forms deliver multiple-doses of medications by a rotating disk or twisting plastic applicators. Each dose is breath actuated when inhaled, after a blister of powder medication is punctured open by a rotating device. Examples include Advair, Serevent, Asmanex inhalers.

Furthermore, a serious problem with these metered devices is suitable means for displaying such features and the number of doses remaining, date or time of last dosage, or other information of necessity and convenience to the user. Display solutions have been unsatisfactory. A common method is to incorporate a mechanical device that counts up or down by changing a mechanical counter each time the dispenser is used. The most serious problem with this approach is that the numbers displayed on the counter are small and difficult to read, particularly by a senior citizen. The mechanical device itself adds weight and bulk to the dispenser making it complicated and difficult to use. Electronic solutions have been equally unsuccessful faced with the same problem of making an easily readable display without altering significantly the size and shape of the delivery device. Unsuccessful electronic solutions have made use of existing LCD displays on bulky glass substrates such as used, for example, in wrist watches. These types of electronic devices also add significant weight and bulk to the existing drug delivery device. The displays with associated electronics, the need for programming and packaging make for bulky dispenser units which pose barriers to the end users.

It would therefore also be useful to provide a new display device for drug dispensers that are conformable to the curved surface of the drug delivery device so that it does not alter its shape and size. Being thin with flexible plastic substrates also adds insignificant weight to the device and most importantly, it provides large readable numbers and images that are updateable and convenient to users of any age. Furthermore, such a display can provide more information than the number of remaining dosages. Such features and the time the last dose was taken, number of doses taken that day, time for inhaler replacement, etc. can be clearly displayed.

Furthermore, as a product for diabetes patients, there are numerous handheld blood glucose meters or monitoring systems on the market today that are designed to make glucose monitoring as simple and convenient as possible. The size and shape of the monitors is important in their design so that they can be portable and easy to use. The size of the monitors is typically around 2×3×½ inches, primarily limited by the flat display inside the monitor to provide the user with the numerical results obtained with a blood glucose strip from blood sample. Major manufacturers of blood glucose meters include: Abbott, Roche, Life Scan, and Bayer. A recent miniature style glucose meter is a OneTouch UltraMini blood glucose monitor device by Lifescan, such as a OneTouch UltraSmart blood glucose monitor by Lifescan. A blood sample is taken for use with current blood glucose meters. Non-invasive blood glucose meters are being developed in which a blood sample does not have to be taken but which instead uses optical interferometer technology to obtain the reading. A limiting feature in the design of the prior art glucose monitors is the display, typically an LCD, due to the need for long battery life. A problem with LCD displays of the prior art is that they are flat and made on rigid glass substrates. This forces the glucose monitoring device to also be flat particularly if the numbers on the display are to be large and easily readable to the user.

It would be useful to provide monitor designs in the shape of a small cylindrical pen that could be carried in the pocket. This is not possible with the current technology having flat rigid LCD displays as the size of large easily visible numeric readouts cannot conform to an average portable pen size. The present invention also allows the conformed film display to be applied to a blood glucose meter in the shape of a watch-like device with wrap around numeric display.

Figure 6:
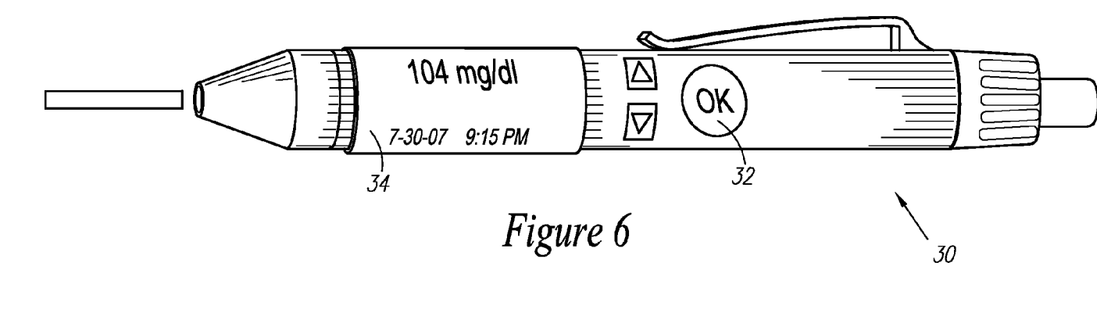
FIG. 6 is an illustration of an example of a pen-shaped blood glucose meter with a conformable thin wrap around film display.

It would also be useful to provide a flexible film display that can be made to conform to the desired shape of the glucose monitor allowing larger numerals for a smaller size device and one that is of a more convenient shape. For example, with the conformable film display a blood glucose meter can be made in the shape and size of a cylindrical pen that is easily carried in the pocket as illustrated in FIG. 6. The film display can wrap around the cylindrical shape of the pen and, as a result, provide larger numerals that are easier to read. In another application the blood glucose meter can be made into a shape of a curved wearable watch-shaped monitoring device, which permits the device to have a large numeric curved display.

It would also be useful to provide a thin flexible display is that it is a bistable technology such that the last reading remains on the display even after the device is turned off. Such a display does not consume electrical power to continually display the image providing for smaller batteries and longer battery life for the monitoring device.

Yet another useful feature could be providing digital readouts that can be displayed in color, providing useful information and features like warning and error message to the user, prompting attention to medical care as needed. It would be further useful to provide a wide viewing angle, so that the display can be observed by multiple individuals which can facilitate user assistance or training.

SUMMARY OF THE INVENTION

Provided are a plurality of embodiments the invention, including, but not limited to, a medication dispensing device comprising: a container for holding a medication; and a color display mounted on the container. The display is adapted for providing an indication of a status of the medication utilizing color, such that the color of the display changes to represent a change in the status of the medication.

Also provided is a color display adapted for being placed on a medication dispensing device, the display comprising: a thin, flexible substrate; an adhesive on the substrate for attaching the display to the medication dispensing device; a power supply; at least one layer of electronics provided on the substrate including electronic components for driving the display; and a plurality of layers provided on the substrate, each one of the layers for displaying a different color. Each one of the layers is comprised of a bistable cholesteric material, such that an image is initially generated for display on the display by using a threshold voltage utilizing the power supply, and wherein the image is subsequently maintained on the display without drawing any substantial current from the power supply.

Further provided is a method of displaying a current status of a medication, comprising the steps of:
providing a container for holding the medication;
providing a flexible color display mounted on the container;
determining a first status of the medication;
indicating the first status of the medication using a first color, wherein the first status is viewable utilizing reflected background light without the use of a backlight and wherein the first status is maintained on the display without the consumption of power;
detecting a change in the status of the medication to a second status; and
indicating the second status of the medication using a second color, wherein the second status is also viewable utilizing reflected background light without the use of a backlight and wherein the second status is maintained on the display without the consumption of power.

Also provide is a medication dispensing device comprising: a container for holding a medication; a sensor or a user input device for obtaining information about a status of the medication; and a color display mounted on the container. The display includes: a thin, flexible substrate; an adhesive on the substrate for attaching the display to the medication dispensing device or container; a power supply; at least one layer of electronics provided on the substrate including electronic components for driving the display, wherein the electronics is connected to the sensor or the user input device; and a plurality of layers provided on the substrate, each one of the layers for displaying a different color. Each one of the layers is comprised of a bistable cholesteric material, such that an image is initially generated for display on the display by using a threshold voltage utilizing the power supply, and wherein the image is subsequently maintained on the display without drawing any substantial current from the power supply. Furthermore, the color of the display is one of yellow, green, blue, red or a combination thereof to reflect a first status of medication, and wherein the color of the display is changed to a different one of yellow, green, blue, or red, or a different combination thereof to reflect a second status of the medication based on the information obtained by the sensor or the user input device.

Also provided are additional embodiments of the invention, some, but not all of which, are described hereinbelow in more detail.

BRIEF DESCRIPTION OF THE DRAWINGS

The features and advantages of the examples of the present invention described herein will become apparent to those skilled in the art to which the present invention relates upon reading the following description, with reference to the accompanying drawings, in which.

DETAILED DESCRIPTION OF THE EXAMPLE EMBODIMENTS

Disclosed is the use of reflective display technologies that can be manufactured on thin, flexible substrates that can be shaped and made to adhere to the surface of a container, such as a pill bottle cap, pill bottle, or a pill dispenser, for example. Also disclosed are such bistable reflective display technologies that can be shaped to conform or wrap around a drug dispenser unit and adhere to a curved surface. These displays can provide large text display, and color displays and backgrounds to aid in the dispensing of the medications found in these types of containers, for example.

A preferred flexible display technology for use in the applications discussed in this disclosure is the bistable cholesteric display technology. Cholesteric displays are highly reflective such that they can be seen in bright daylight or a dimly lit room. Because cholesteric liquid crystals can be made to be bistable, they can be made to require power only when being addressed (e.g., when updating the displayed image), further adding to the power savings associated with such displays and weight savings due to smaller battery sizes.

Cholesteric liquid crystalline materials are unique in their optical and electro-optical features. Of principal significance, they can be tailored to reflect light at a pre-selected wavelength (color) and bandwidth. Light polarizing materials are not needed in contrast to other LCD technologies, reducing the cost and improving the brightness. Bright, iridescent images such as numbers, text, icons, or images can be electronically updated; color as well as shades of gray are also available. Manufactured on thin flexible plastic substrates, this low power electronic technology can be useful for use on handheld devices. Such portable devices tend to require only very small batteries, as the display consumes very little power. Cholesteric displays, therefore, are ideal for the applications disclosed herein, as the bistability feature avoids the need for refreshing power and the high reflectivity avoids the need for power-consuming backlights. Like ink on paper, reflective displays are also easily read in nearly any lighting condition, further improving their utility. The wide view angle offered by a cholesteric display allows several persons to see the display image at the same time from different positions, and allows the device to be operated in many orientations with the display being readable. Fundamental aspects of such cholesteric displays using cholesteric materials possessing a positive dielectric anisotropy are disclosed in, for example, U.S. Pat. Nos. 5,437,811 and 5,453,863, incorporated herein by reference.

Bistable cholesteric liquid crystal displays have a distinctive electronic drive feature that other bistable reflective technologies do not: a voltage threshold. This can be important for a display even with moderate resolution in addressing a matrix of many pixels. A threshold voltage is utilized for multiplexing a row/column matrix without the need of an expensive active matrix arrangement (e.g., transistor at each pixel), and thus the drive electronics (i.e., driver) can be simplified and miniaturized, and its power consumption reduced. Bistability with a voltage threshold allows high-resolution displays to be multiplexed and produced with low-cost passive matrix technology.

Multiple color cholesteric displays are currently made by either stacking three displays of each primary color, red, green and blue on top of one another (e.g., U.S. Pat. No. 6,377,321, incorporated by reference) or by color patterning each pixel with red, green and blue reflective areas (e.g., U.S. Pat. No. 5,668,614, incorporated by reference).

Other bistable reflective technologies suitable for thin flexible displays for drug delivery devices include such technologies as electrophoretic displays, electrochomic displays, smectic displays and a variety of bistable TN types. While these other bistable technologies are a possible alternative for the applications discussed herein, they do not have all of the combined features of bistable cholesteric displays such as muliplexibility, low current, polarizer free, and suitability for low cost continuous roll manufacturing, and thus are likely less desirable.

In addition to bistable cholesteric displays with liquid crystalline materials having a positive dielectric anisotropy, it is possible to fabricate a cholesteric display with liquid crystalline materials having a negative dielectric anisotropy as, for example, described in the U.S. Pat. No. 3,680,950 to Haas et al., or 5,200,845 to Crooker et al., both incorporated herein by reference. These "negative materials" like the "positive" materials are chiral nematic liquid crystals that are prepared from nematic materials that have been twisted into a helical molecular arrangement by the addition of chiral compound or collection of chiral compounds. The negative and positive materials are prepared from nematic liquid crystals with either a negative or positive dielectric anisotropy respectively.

Negative type cholesteric displays can operate in a bistable mode where the material is switched into the stable planar (e.g., color reflective) texture with an AC pulse, or into the stable focal conic (e.g., transparent) texture with a DC pulse, as described by U.S. Pat. No. 3,680,950, incorporated by reference. There are other modes of operation such as has been disclosed by Crooker where a droplet dispersion of negative cholesteric materials is switched into the planar, color reflective texture with an applied electric field, but relaxes back into a transparent texture when the field is removed.

Some cholesteric materials possess a dielectric anisotropy that can be negative under an applied electric field of one frequency but positive at another frequency. This feature can be used to drive a bistable display using a dual frequency drive scheme, such as that described in U.S. Pat. No. 6,320,563, incorporated herein by reference.

Flexible displays are also disclosed in U.S. Pat. No. 5,751, 257 (disclosing a two-substrate flexible cell design for a shelf tag with a contact strip connected to the display electrodes with external electronic drive electronics are connected to the display through the contact strip); U.S. Pat. No. 4,948,232 (using a contact strip to connect a large format two-substrate flexible display to external drive apparatus); U.S. Pat. No. 4,896,946 (disclosing a two-substrate flexible display connected to a circuit board via conductive adhesive contact strip); U.S. Pat. No. 6,864,435 (disclosing a display design for a flexible smart card where conductors on the back surface of the display substrate are connected to integrated driver and other circuits as well as the column electrodes on the top side of the substrate via holes filled with a conductive material); U.S. Patent Application Publication No. 2003/0202136 (disclosing a cholesteric liquid crystal display fabricated on a single flexible transparent substrate); and U.S. patent application Ser. No. 11/228,137 (disclosing a display that is coated or printed in layers directly onto a printed circuit board); all of which are incorporated herein by reference.

Accordingly, the above display technologies, among others, can be utilized for the applications discussed in more detail in the remainder of this disclosure. Referring now to various embodiments of the invention, one application features a drug dispenser including an updateable electronic display film (such as of the types discussed above) shaped to conform to the container. The drug dispenser can be any container adapted to contain pharmaceuticals such as in pill form (e.g., a pill bottle). The display film can be placed on a cap of the container, for example. One embodiment of the invention features the display film being a bistable cholesteric display. Other embodiments of the invention feature the display being an electrophoretic display, a smectic display, an electrochromic display or a bistable TN display, for example. In another embodiment, the display is in the form of numeric or alphanumeric digits. The digits can indicate the number or amount of doses, pills, or drug quantity remaining in the drug container, and/or when a dosage was last taken or needs to be next taken (e.g., date/time).

The display can also be provided to produce multiple colors, and thus can be utilized to indicate information by changes in color, instead of, or in addition to, using text. For example, the display might show a red display when a dose has been recently taken (and thus no dose is immediately due), a yellow display when a dosage is nearly due (or just past due), and a green display when a dose is due to be taken. Alternatively, a display might be black when no dosage is due, green when a dosage is due, yellow when a dosage is just past due, and red when a dosage is long past due. Further alternatives might just utilize two colors (such as red and green), or might utilize additional or different colors (e.g., red, green, yellow, black). The use of colors can help those whose poor eyesight makes it difficult to read text or numbers, and can help those who may have difficulty understanding the English (or any other) language, or who may even be illiterate.

The display can indicate the current time, the time when the last dosage was taken, the time when the next dosage is due, and/or when the drug has expired or is going to expire. Such an embodiment might utilize an electronic clock as part of the electronics of the display to track time. The drug dispenser display may have other functions and features that would be apparent to one skilled in the art in view of this disclosure.

Furthermore, text and color can be combined in numerous ways for emphasis. For example, black text can be used on color backgrounds, with the backgrounds emphasizing the instructions provided by the text (e.g., green background with instructions to take dosage of medication now). Alternatively, rather than using background colors, the text itself might be provided in color, such as in a scheme discussed above. Using colored text and differently colored backgrounds could be utilized to increase contrast, or indicate specialized conditions, for example.

Figure 1:
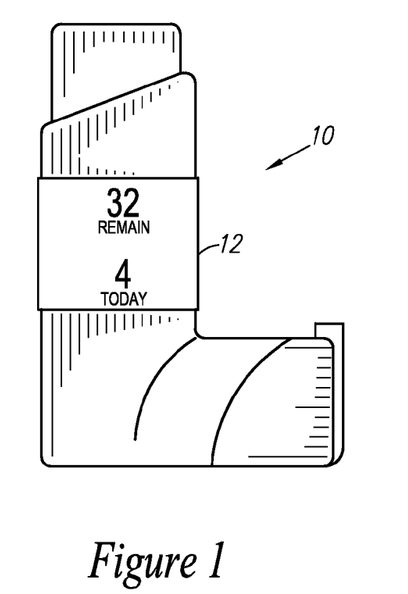
FIG. 1 is an illustration of an example of a drug delivery device with an inventive conformable display.
Figure 2:
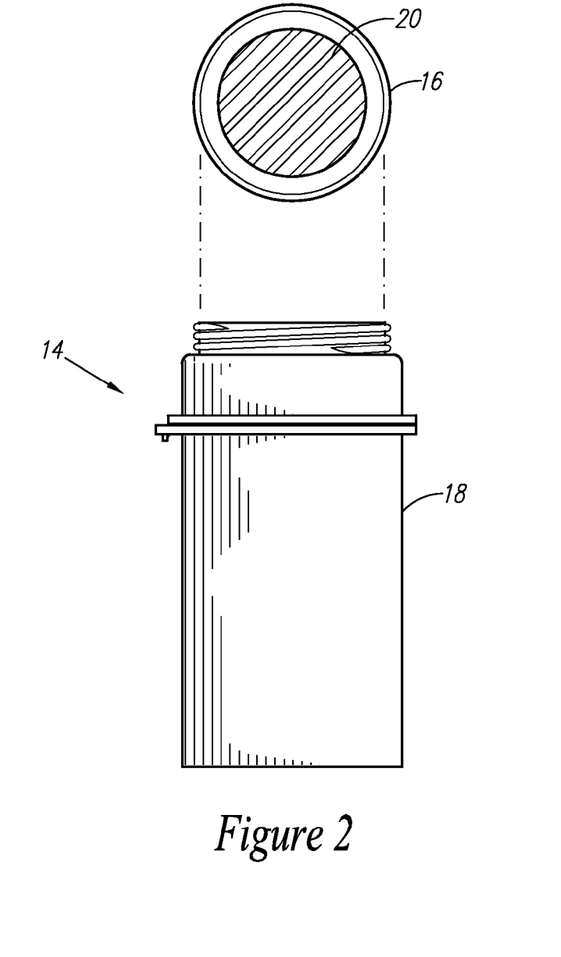
FIG. 2 is an illustration of an example of a pill bottle with cap containing a film display shaped to conform to the cap surface displaying images with changing color.

FIG. 2 is an illustration of a pill bottle container 14 including a body 18 and a cap 16, with a display 20 mounted directly on a surface of the cap 16 and conforming to the circular shape and curvature of the cap 16. This display 20 could be a thin, conformable, bistable reflective display, as discussed above. As illustrated, the flexible display 20 is attached to a part of the device 14, such as by using an adhesive such as a glue or other sticky substance to the device, much as a paper label might be attached to a traditional pill bottle. The display 20 on the cap 16 can display different colors, numerals, letters, words or other images as is needed to remind a user when to take a pill. Of course, the display could be provided on the body 18 of the bottle 14, such as by using a wrap-around display that can conform to the curved portion of the bottle (as discussed in more detail with respect to the embodiment of FIG. 1, below).

Figure 3A:
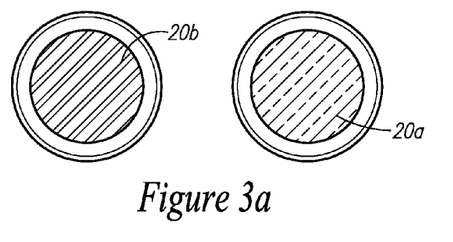
FIG. 3 is an illustration of an example of a display film on pill bottle cap patterned with two different colors and two colors with black.
Figure 3B:
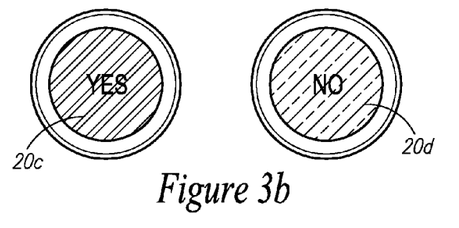

FIGS. 3a and 3b illustrate examples of a display that is switched between two colors (for example, green and red), with FIG. 3a representing a red display status 20a and a green display status 20b. The display switches at times to indicate a particular status, such as when a pill is to be currently taken (e.g., green, 20b) and when it is not time to take a pill (e.g., red, 20a). The pill bottle display may simply change color as illustrated in FIG. 3a, or may also display words, such as illustrated in FIG. 3b, showing an example where the words are in black and the words and colors correspond, in order to emphasize the current status (e.g., 20d: "no" with red background to indicate no pill is to be taken, and 20c: "yes" with green background indicating that a pill is due to be taken). Images may also be shown in addition to, or instead of, the text, or text might be utilized without background colors. Alternatively, color could be used for the text instead of the background, or in addition to the background. Such a display can be fabricated by stacking two bistable cholesteric films such a red file and green film. Such a display solution is disclosed, for example, in U.S. Pat. No. 6,377,321. Words or images may be displayed by a passive matrix, row and column design of the electrodes or by a segmented design of electrodes as is known in the art of liquid crystal displays, or by using icons.

Figure 4A:
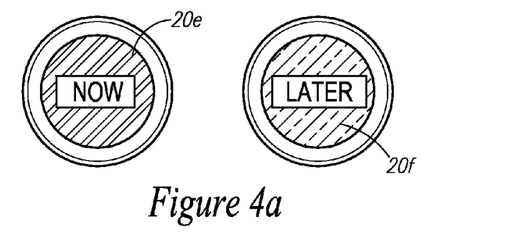
FIG. 4 is an illustration of an example of a display film on pill bottle cap patterned with three different colors and three colors with black.
Figure 4B:
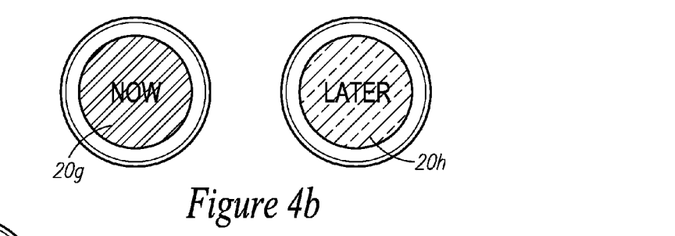
Figure 5:
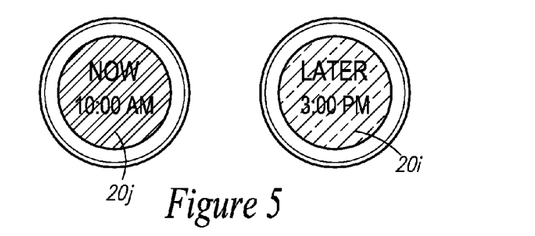
FIG. 5 is an illustration of an example of a display film on pill bottle cap patterned with two different colors indicating time.

FIGS. 4a and 4b illustrate examples of a display that can be used to show three colors. FIG. 4a illustrates an example of using three colors, red, green and yellow, with reminder words in black. For example, display status 20e is used to indicate that it is time to take a pill, with the hashed area providing a green background, the rectangle providing a yellow background, and the word "now" provided in black text. In contrast, display status 20f indicates that it is not yet time to take a pill, providing a red background, with the rectangle again providing a yellow background and the word "later" also being in black text. FIG. 4b illustrates another example where the words are shown in color (e.g., yellow) against the green or red background (20g and 20h, respectively), without using the special text background color. Of course, different color schemes can be utilized, and may be provided as different options depending on the type of drug or the intended user, or the particular status types to be indicated (such as when a refill of the medication may be nearly due, when the medication may be near its expiration date, when the medication may have been tampered with, etc.). Again, this display can be fabricated by the bistable cholesteric stacking method as, for example, disclosed in U.S. Pat. No. 6,377,321 with passive matrix or segmented electrodes. FIG. 5 shows an illustration of an example where the time of the display is also shown (see 20j and 20i).

In one embodiment of this disclosure, the pill cap display is switched with time. The display control electronics keeps track of the time in order to remind the user when it is time to take a pill. The cap can be pre-programmed, or it may be programmed by the pharmacist (such as by using a specialized device, that might connect to the display by wired or wireless technology). The device could be programmed for the times during the day in which a pill is to be taken, for example. This programming might include relatively complicated logic, such as special indications for when a dosage was missed (e.g., whether the dose should be immediately made up, or delayed, etc.). In another embodiment, a switch can be provided on the cap (or elsewhere on the bottle) that is triggered when the pill bottle cap is removed, or when a pill is removed, using available electronic technology. This can be used as a means for reminding the user if or when a pill has been taken, tracking the number of pills taken, etc. In yet another embodiment, the time and a cap removal switch are used in combination to keep track of the time and indicate and track when the cap has been removed to take a pill. The control electronics may also monitor the number of times a cap has been removed and the time last removed. Other embodiments such as a button for the user to indicate when a pill is taken are also possible. The device might track if too many pills are removed for a dose, or not enough pills are removed. The display might even store information for later retrieval by the pharmacist or a doctor for aid in tracking the patients use of the medication.

There are at least three different ways to construct a bistable cholesteric display exhibiting different colors. One method is in which cholesteric reflective materials of different color are laminated, coated or otherwise layered on top of one another to create the multi-colored display. The colors then additively mix to provide a desired resultant color in the same area of the display by light traveling through the display (such as by being reflected off the substrate or other background). Gray scale capability of the bistable cholesteric technology allows a broad variety of different colors, including different shades. For example, two cholesteric layers provide for four different colors without gray scale, but can provide many more shades of colors with the use of gray scale, depending upon the total number of shades of gray that can be provided by the drive electronics. The three color layers composed of the three primary colors, Red, Green and Blue (RGB), for example, provide eight colors without shades of gray, and as many a 4096 colors with 16 shades of gray. With stacked layers, therefore, one may considerably simplify the design of the display in that color can replace images as reminders.

Another method to achieve multiple color display is by use of a single bistable cholesteric layer that is patterned. In this embodiment, the reflective color of the cholesteric material is patterned by a means such as described, for example, in U.S. Pat. No. 5,668,614 (incorporated by reference). These colors occupy different areas of the display, but can combine to create a colored effect. This means of producing multiple-color has advantages in cost and manufacturing simplicity in electronic interconnects.

A third approach of achieving color uses two preselected colors areas determined by the reflective color chosen for the reflective texture of the cholesteric liquid crystal, and the color chosen for the back plane of the display. The colors of the display then switch between the color of the backplane, and the color created by additive mixing the cholesteric reflective texture with the backplane, as described in U.S. Pat. No. 5,493,430, incorporated by reference.

A fourth approach to providing a multiple colored display is by voltage control of the color, as has been described in the IDRC 06 Conference held a Kent State University in October 2006.

The transparent conducting electrodes of the display may be patterned in segments for alphanumeric or numeric readouts, or as special images and/or icons. More preferably, the electrodes may be patterned as rows and columns typical of a passive matrix, so that the image is created by software stored within an electronic memory provided with the display electronics.

Another feature of the inventive technology is that the associated drive electronics (including any memory, processor, etc.) can also being printed or otherwise mounted on the thin flexible substrate of the conformable display, leading to a compact, integrated solution.

For example, a display can be manufactured directly onto the non-component side of a flexible printed circuit board (PCB). The display could be provided as a stacked sequence of coated, printed, or otherwise laminated layers that form a film with all the elements of a reflective display such as the liquid crystal material, transparent conducting electrodes, insulation layers to prevent electrical shorts and isolate components, and any needed protective layers, all stacked together in a veneered film forming all the elements of a display. The layers can each be cast, for example, in sequence onto the non-component side of the PCB containing the driving electronics. Rugged connections to the display are made automatically, as the conducting layers of the display cell are applied to exposed contacts or vias on the non-component side of the PCB (see U.S. patent application Ser. No. 11/228, 137, publication number 2007/0063939, incorporated by reference). The advantages are a simplified LCD manufacturing process at lower cost resulting in a much more rugged construction eliminating fragile interconnection cables/tabs typical of prior art electronic display technology.

Cholesteric materials are particularly well suited for flexible display processing in that they can be encapsulated as droplet dispersions that can be coated or printed and are self-sealing to contain the cholesteric liquid crystal in the film. Furthermore, cholesteric materials are field driven requiring near negligible current to change their optical state. As such, the conducting electrodes can be materials as conducting polymers or carbon nanotubes that can be printed or coated into a film greatly reducing the number of steps in display processing compared to prior art of producing indium tin oxide, ITO, electrodes.

General aspects of the invention feature a drug delivery device with an electronic display that conforms to the shape of the device. The drug delivery device can be any device for dispensing medication including an inhaler (e.g., metered drug inhaler or dry powder inhaler). The electronic display can be a bistable cholesteric display. Other aspects of the invention feature the display being an electrophoretic display, smectic display, electrochromic display or bistable TN display. The display can be in the form of a flexible film for conforming to shape of the drug delivery dispenser. The display can produce multiple colors. In another aspect the display is in the form of numeric digits. The digits can indicate the number of remaining doses in the drug container, the amount of drug remaining in the container and/or when dosage was last taken (e.g., date/time). The display can indicate information by changes in color. The display can indicate the time, the time when the last dosage was taken and/or when the drug has expired. The drug dispenser display may have other functions and features that would be apparent to one skilled in the art in view of this disclosure.

In addition to using a display on a pill bottle, a display could be beneficial in use for metered dose inhalers. In traditional approaches, there is a problem of using a mechanical display on a drug delivery inhaler device, such as dose counters on metered dose inhalers (Albuterol®, Proair®, Flovent® Qvar MDI's) and counters on dry powder inhalers (Advair®, Asmanex®, and Serevent®). A mechanical numerical readout not only adds to the bulk of the device, but also provides a small sized numerical digit difficult if not impossible to read by many users; e.g., senior citizens. A traditional LCD display is not a significant improvement, because the bulkiness that it adds to a delivery device, and also because of a small display readout.

FIG. 1 is an illustration of an inhaling device 10 with a thin, conformable display 12 (such as a bistable reflective display) mounted directly on the device 10, with the display conforming to the cylindrical curvature of the drug delivery device. As illustrated, the flexible display can be glued to the device, much as a piece of paper. Large readable digital numerical readouts can be provided that are clearly visible with this display technology. Another feature of the inventive technology is that, as discussed above, the associated drive electronics can also be printed or otherwise mounted on the thin flexible substrate of the conformable display.

The inventive dispenser display can come in different formats depending upon its use, and can incorporate the various features discussed above for the pill bottle display. When only a number is to be displayed, the display electrodes can be segmented to display numeric or alphanumeric characters or symbols. In other cases, it may be desired to have the display electrodes patterned in the form of a matrix so that the display may be more versatile to interchangeably display words, or a picture or numbers or symbols. The display may also be in multiple-color so that color or changes in color may be used to provide information to the user. The inventive conformable dispenser display adds features to the inhaler not possible before.

As an additional example, a medical device inhaler (MDI) display was built using polymerization induced phase separation (PIPS) process. The display was built from two substrates which were 2 mil Dupont Tejin HLA polyethylene terephalate (PET) coated with 200 ohm/sq ITO. The ITO coatings were patterned such that each pixel is individually directly driven. The pattern of the pixel segments creates a display that counts down the number of prescription inhalations remaining in the device. In order to enable the device to be conformed to a specific curvature, encapsulation of the ChLC was required. A PIPS encapsulating material was made using the cholesteric liquid crystal mixture KLC19 (Kent Displays, Inc.) with the encapsulating polymer formulation as described in U.S. Pat. No. 7,351,506 (incorporated by reference) using a functionality of, F=1.2 with an exposure to ultraviolet radiation of intensity 0.92 mW/cm$^2$ for 20 minutes. The spacers are 4 μm Micropearl plastic spheres from Sekisui Chemical Co., Ltd. The ChLC and polymer mixture was laminated between the substrates identified above. The monomer polymerizes and the ChLC phase separates from the polymer creating encapsulated droplets of liquid crystal surrounded by shells of polymer. The display is bonded to a flex circuit using anisotropic conductive film from 3M. The flex circuit connects to a PCB containing the drive electronics. The display is conformed to a specific curvature and placed into the MDI case along with the PCB, and can be used to indicate the number of remaining dosages of medication available, for example.

Additional applications for the display discussed herein include their use in glucose monitoring devices. There is a problem of using a flat LCD glass display on a blood glucose monitoring device. The flat rigid display typically controls the shape and size of the monitor, limiting the design of the monitor. The numerical and other images on the display need to be large enough to be conveniently read. When incorporating a flat rigid display, this significantly limits the shape and size of the monitor design. Some LCD glass displays do have limited back lighting, but in order to limit electrical power consumption and to increase the lifetime of the battery, reflective images are typically displayed only in black and grey, not providing bright color images that could be used to aid in communication of warning or error messages of the monitor or other convenient indicators to the user.

Figure 7:
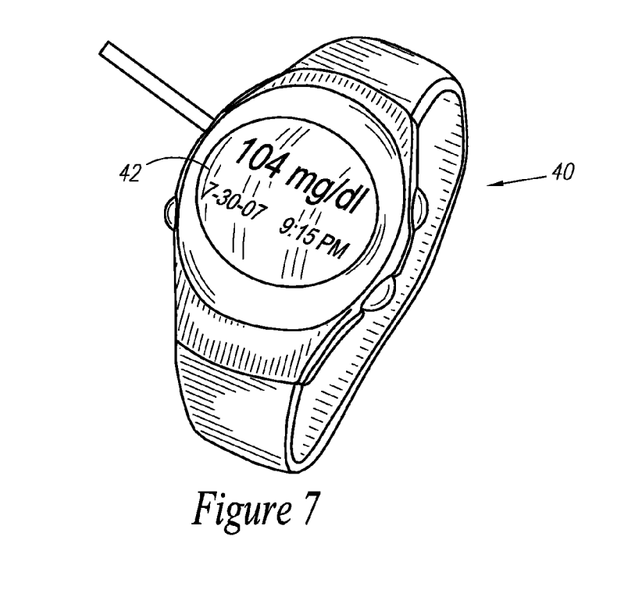
FIG. 7 is an illustration of an example of a watch-shaped blood glucose meter with a conformable thin wrap around film display.

FIGS. 6 and 7 illustrate blood glucose monitoring systems in the shape and size of a pen 30 or watch 40 with a thin conformable bistable reflective displays 32, 34, and 42 mounted directly on the devices, conforming to the curvature of the devices. As illustrated, the flexible displays can be glued to the device, much as a piece of paper, or otherwise mounted. Large readable digital numerical readouts are clearly visible with this display technology, and color can be provided as discussed above, to indicate various status information.

Another feature of the inventive technology is the associated drive electronics also being printed or otherwise mounted on the thin flexible substrate of the conformable display, as also discussed above.

The invention has been described hereinabove using specific examples and embodiments; however, it will be understood by those skilled in the art that various alternatives may be used and equivalents may be substituted for elements and/or steps described herein, without deviating from the scope of the invention. Modifications may be necessary to adapt the invention to a particular situation or to particular needs without departing from the scope of the invention. It is intended that the invention not be limited to the particular implementations and embodiments described herein, but that the claims be given their broadest interpretation to cover all embodiments, literal or equivalent, disclosed or not, covered thereby.

What is claimed is:

1. A medication dispensing device comprising:
a container for holding a medication; and
a reflective color display mounted on said container, wherein said display is adapted for providing an indication of a first status of said medication by displaying a first color, such that the color displayed by said display changes to displaying a second color to represent a change in the status of said medication to another status.

2. The device of claim 1, wherein said display is a bistable color display provided with a thin, flexible substrate.

3. The device of claim 2, wherein said display conforms to a curve in said container.

4. The device of claim 3, wherein said container includes a cylindrical component, and wherein said display is wrapped around a substantial portion of said cylindrical component.

5. The device of claim 4, wherein said display acts as a label for said device, and wherein said display is attached to said cylindrical component using an adhesive.

6. The device of claim 2, wherein said container includes a removable cap, and wherein said display is provided on said removable cap.

7. The device of claim 1, wherein said display further provides an indication of the status of said medication by also using alphanumeric or numeric text.

8. The device of claim 7, wherein said color of a status of said medication is reflecting in the color of said text.

9. The method of claim 1, wherein the first color of said display is one of yellow, green, blue or red to reflect the first status of said medication, and wherein the color of said display is a different one of yellow, green, blue, or red to reflect a second status of said medication.

10. The device of claim 1, wherein said display utilizes reflected light for viewing said indication without any active backlight such that said color is maintained on said display absent a change in status without consuming power.

11. The device of claim 1, wherein said display is a bistable cholesteric color display.

12. A color display adapted for being placed on a medication dispensing device, said display comprising: a thin, flexible substrate; an adhesive on said substrate for attaching said display to said medication dispensing device; a power supply; detection component for detecting any of a plurality of states of said medication dispensing device; at least one layer of electronics provided on said substrate including electronic components for driving said display; and a plurality of layers provided on said substrate, each one of said layers for displaying a different color, wherein each one of said layers is comprised of a bistable cholesteric material, such that an image is initially generated for display on said display by using a threshold voltage utilizing said power supply, and wherein said image is subsequently maintained on said display without drawing any substantial current from said power supply, and wherein said display associates a different one of said colors for display according to different ones of said states of said medication dispensing device that are detected by said detection component, wherein said display utilizes reflected light reflected off said substrate for viewing said image without any active backlight.

13. The color display of claim 12, wherein said display is adapted for installation on a removable cap of said medication dispensing device or container.

14. The color display of claim 12, where said display is adapted for installation on a curved surface of said medication dispensing device or container, such that said display conforms to said curved surface.

15. The display of claim 12, wherein the color of said display is one of yellow, green, blue or red to reflect a first status of medication, and wherein the color of said display is a different one of yellow, green, blue, or red to reflect a second status of the medication.

16. A method of displaying a current status of a medication, comprising the steps of:
    providing a container for holding said medication;
    providing a flexible color display mounted on said container;
    determining a first status of said medication;
    indicating said first status of said medication using a first color, wherein said first status is viewable utilizing reflected background light without the use of a backlight and wherein said first status is maintained on said display without the consumption of power;
    detecting a change in the status of said medication to a second status; and
    indicating said second status of said medication using a second color, wherein said second status is also viewable utilizing reflected background light without the use of a backlight and wherein said second status is maintained on said display without the consumption of power.

17. The display of claim 16, wherein said first color is one of yellow, green, blue or red to reflect a first status of medication, and wherein the color of said display is a different one of yellow, green, blue, or red to reflect a second status of the medication.

18. The display of claim 16, wherein power is consumed by said display when initially generating said indication of the first status and when initially generating said indication of the second status.

19. The display of claim 16, wherein said display is mounted on a cap of said container using an adhesive.

20. The display of claim 16, wherein said display is mounted a curved surface of said container using an adhesive, such that said display conforms to said curved surface.

21. A medication dispensing device comprising: a container for holding a medication; a sensor or a user input device for obtaining information about a status of the medication; and a reflective color display mounted on said container, said display including: a thin, flexible substrate; an adhesive on said substrate for attaching said display to said medication dispensing device or container; a power supply; at least one layer of electronics provided on said substrate including electronic components for driving said display, wherein said electronics is connected to said sensor or said user input device; and a plurality of layers provided on said substrate, each one of said layers for displaying a different color, wherein each one of said layers is comprised of a bistable cholesteric material, such that an image is initially generated for display on said display by using a threshold voltage utilizing said power supply, and wherein said image is subsequently maintained on said display without drawing any substantial current from said power supply, and wherein the color of said display is one of yellow, green, blue, red or a combination thereof to reflect a first status of medication, and wherein the color of said display is changed to a different one of yellow, green, blue, or red, or a different combination thereof to reflect a second status of the medication based on said information obtained by said sensor or said user input device.

22. A medication dispensing device comprising:
    a container for holding a medication; and
    a bistable color display mounted on said container for displaying a plurality of colors using reflected light, wherein
    said display is a cholesteric display and is adapted for providing an indication of a first status of said medication utilizing a first one of said colors displayed by said display, and wherein
    said display is adapted for providing an indication of a second status of said medication utilizing a second one of said colors displayed by said display.

23. A method of displaying a current status of a medication, comprising the steps of:
    providing a container for holding said medication;
    mounting a color cholesteric liquid crystal display on said container, said display including stacked liquid crystal layers or regions in a single liquid crystal layer, each of said layers and said regions being adapted to reflect light of a different color than another of said layers or said regions, respectively;
    determining a first status corresponding to: a first time, or a first amount of medication in said container;
    indicating said first status by displaying a first color on said display,
    detecting a change in status of said medication to a second status corresponding to: a second time resulting from a passing of time since said first time, or a second amount of medication in said container that is less than said first amount; and
    indicating said second status by displaying a second color on said display,
    wherein said first color and said second color are displayed with light reflected from said liquid crystal using at least one of planar, focal conic and grayscale textures, all of said textures being stable in an absence of an electric field.

24. The device of claim 1, wherein said change in status comprises at least one of the following:
    that another dose of the medication is due to be taken;

the arrival or near arrival of an expiration date of the medication;

that a dose of the medication has recently been taken;

that a dose of the medication is just past due being taken;

that a dose of the medication is long past due being taken; and/or an indication that a container holding the medication is empty or is nearly empty.

25. The device of claim 12, wherein said display is adapted for providing an indication of a status of said medication utilizing color, such that the color of said display changes to represent a change in the status of said medication.

26. The device of claim 25, wherein said change in status comprises at least one of the following:

that another dose of the medication is due to be taken;

the arrival or near arrival of an expiration date of the medication;

that a dose of the medication has recently been taken;

that a dose of the medication is just past due being taken;

that a dose of the medication is long past due being taken; and/or an indication that a container holding the medication is empty or is nearly empty.

27. The device of claim 16, wherein said first status includes that a dose of the medication was properly taken, that the medication is not expired, or that a sufficient amount of medication is available in a container holding the medication, and wherein the second status comprises at least one of the following:

that the next dose of the medication is due to be taken;

the arrival or near arrival of an expiration date of the medication;

that a dose of the medication is just past due being taken;

that a dose of the medication is long past due being taken; and/or an indication that a container holding the medication is empty or is nearly empty.

28. The device of claim 21, wherein said first status is that a dose of the medication was properly taken, that the medication is not expired, or that a sufficient amount of medication is available in a container holding the medication, and wherein the second status comprises at least one of the following:

that the next dose of the medication is due to be taken;

the arrival or near arrival of an expiration date of the medication;

that a dose of the medication is just past due being taken;

that a dose of the medication is long past due being taken; and/or an indication that a container holding the medication is empty or is nearly empty.

29. The device of claim 22, wherein said first status is that a dose of the medication was properly taken, that the medication is not expired, or that a sufficient amount of medication is available in a container holding the medication, and wherein the second status comprises at least one of the following:

that the next dose of the medication is due to be taken;

the arrival or near arrival of an expiration date of the medication;

that a dose of the medication is just past due being taken;

that a dose of the medication is long past due being taken; and/or an indication that a container holding the medication is empty or is nearly empty.

30. A medication dispensing device comprising:

a container for holding a medication; and a reflective color display mounted on said container, wherein said display is adapted for providing an indication of a plurality of statuses of said medication utilizing different colors, such that the color of said display changes to represent a change in the status of said medication, and wherein said status indicated by said display includes indicating that a dose of medication is due to be taken or is past time to be taken.

31. A medication dispensing device comprising:

a container for holding a medication; and a reflective color display mounted on said container, wherein said display is adapted for providing an indication of a status of said medication utilizing color, such that the color of said display changes to represent a change in the status of said medication, and wherein said status indicated by said display includes indicating that a container holding the medication is empty or is nearly empty.

32. A medication dispensing device comprising:

a container for holding a medication;

a device for detecting at least one state of said container; and a reflective color display mounted on said container, wherein said display is adapted for providing an indication of a first status of said medication by continuously displaying a first color, and wherein upon detection of said at least one state, said display is further adapted for providing an indication of a second status of said medication by continuously displaying a second color different than said first color.

* * * * *